United States Patent
Schlaeppi et al.

(10) Patent No.: US 8,902,433 B2
(45) Date of Patent: Dec. 2, 2014

(54) DEVICE AND METHODS FOR CARTRIDGE DETECTION

(75) Inventors: Andreas Schlaeppi, Toffen (CH); Jean-Noel Fehr, Neuchatel (CH); Stefan Lindegger, Huttwil (CH)

(73) Assignee: Roche Diagnostics International AG, Rotkreuz (CH)

( * ) Notice: Subject to any disclaimer, the term of this patent is extended or adjusted under 35 U.S.C. 154(b) by 949 days.

(21) Appl. No.: 12/948,385

(22) Filed: Nov. 17, 2010

(65) Prior Publication Data
US 2011/0286008 A1    Nov. 24, 2011

(30) Foreign Application Priority Data
Nov. 18, 2009  (EP) .................................... 09176362

(51) Int. Cl.
*G01B 11/14*    (2006.01)
*A61M 5/145*   (2006.01)

(52) U.S. Cl.
CPC ..... *A61M 5/1456* (2013.01); *A61M 2205/6063* (2013.01); *A61M 2205/14* (2013.01)
USPC ............................ 356/614; 356/620; 356/622

(58) Field of Classification Search
CPC ..... G11B 15/675; G11B 15/68; G11B 23/107
USPC .......................................... 356/614, 620–622
See application file for complete search history.

(56) References Cited

U.S. PATENT DOCUMENTS

| | | | |
|---|---|---|---|
| 4,599,219 A * | 7/1986 | Cooper et al. | 356/39 |
| 5,917,602 A * | 6/1999 | Bonewitz et al. | 356/614 |
| 2005/0163022 A1* | 7/2005 | Kawasaki | 356/614 |

FOREIGN PATENT DOCUMENTS

| | | |
|---|---|---|
| WO | 2004047641 A2 | 6/2004 |
| WO | 2005097252 A2 | 10/2005 |
| WO | 2006021295 A1 | 3/2006 |

OTHER PUBLICATIONS

Search Report for Application No. 09176362.3-1257 dated May 20, 2010.

* cited by examiner

*Primary Examiner* — Tarifur Chowdhury
*Assistant Examiner* — Iyabo S Alli
(74) *Attorney, Agent, or Firm* — Dinsmore & Shohl LLP

(57) ABSTRACT

The present disclosure relates to an accommodating device for a dispensing or infusion device, comprising: a displaceable element which is displaced within the accommodating device when a cartridge is inserted into the accommodating device; and at least one sensor which can detect the presence or absence of the displaceable element or a detection element disposed on or in the displaceable element.

17 Claims, 18 Drawing Sheets

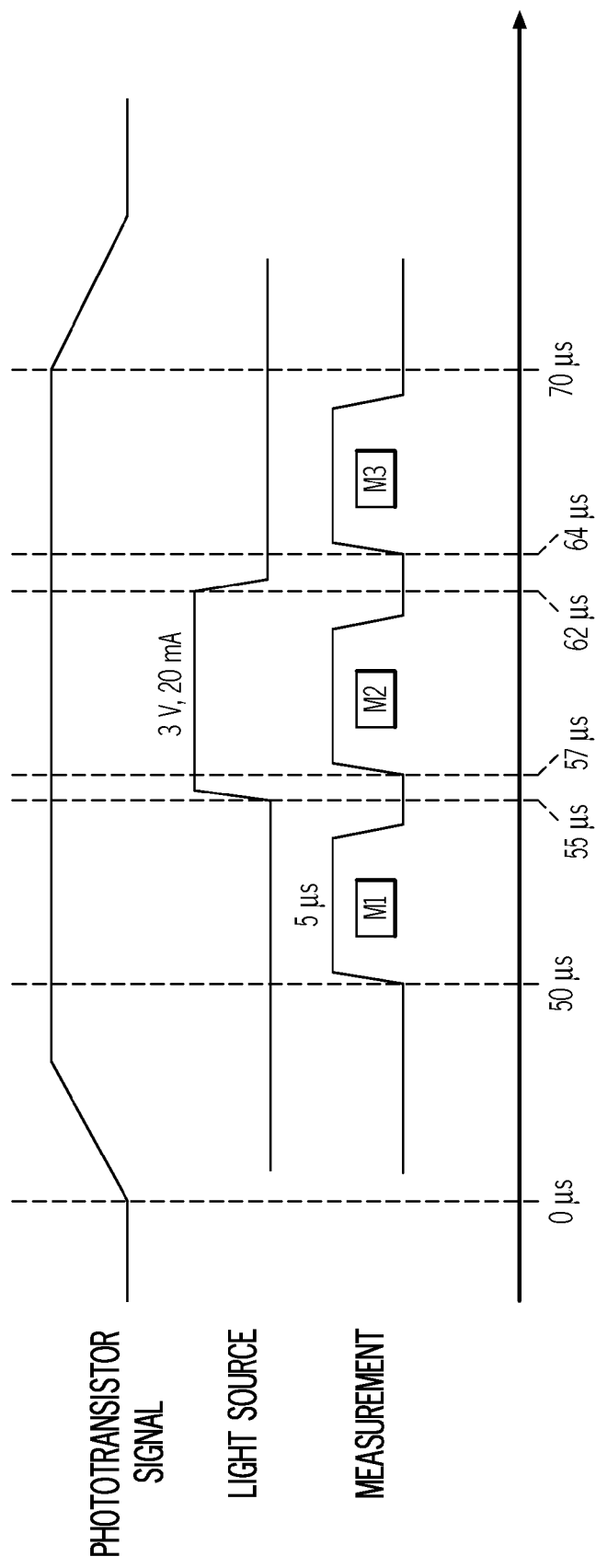

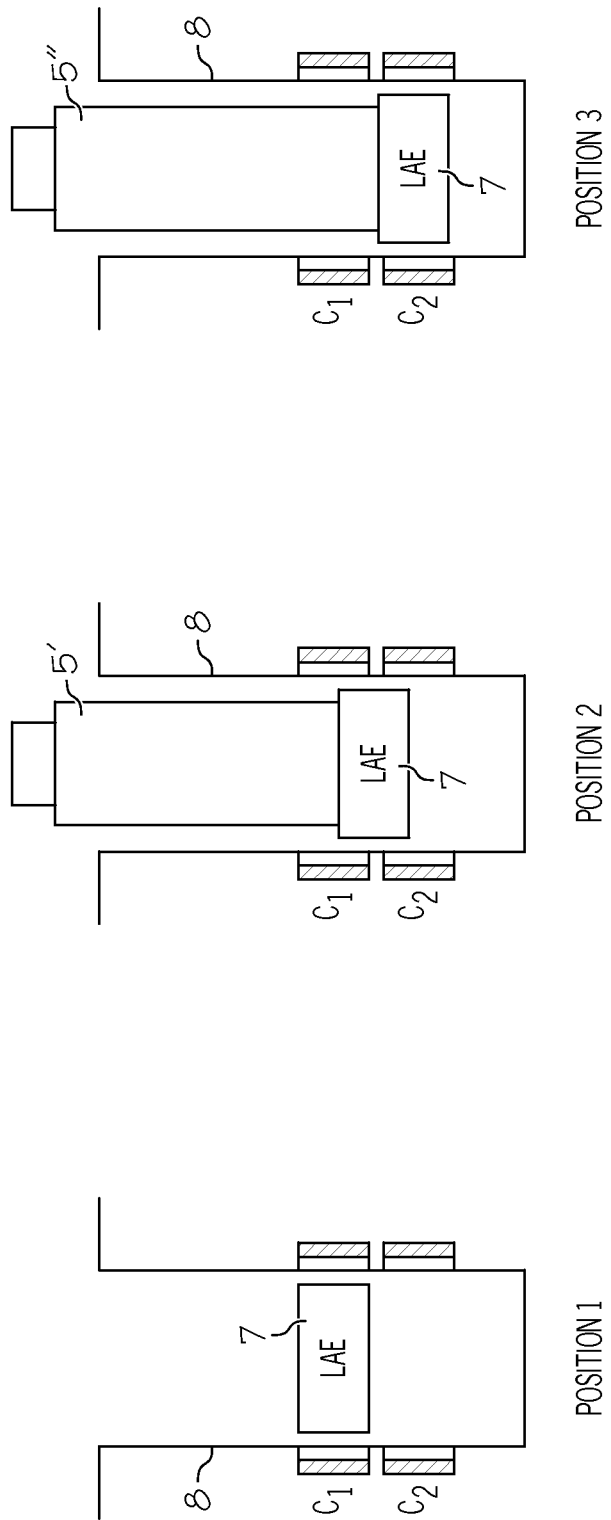

DEVICE AND METHODS FOR CARTRIDGE DETECTION

CROSS-REFERENCE TO RELATED APPLICATIONS

This application claims the benefit of European application EP09176362.3 filed Nov. 18, 2009, which is herein incorporated fully by reference.

TECHNICAL FIELD

The present disclosure relates to a device and method for detecting the presence of a cartridge or a container, in particular detecting whether or not a cartridge is present in a dispensing or infusion device, and detecting the type of cartridge which has been inserted. The present disclosure also relates to a method for operating a device.

BACKGROUND

Delivery devices using replaceable containers have found widespread use, especially in the medical field for delivering a substance contained in a cartridge such as, for example, insulin or growth hormones. A replaceable container or cartridge can be inserted into a reusable pump for a controlled delivery of the substance contained within the container or cartridge. The reusable pump is often designed to be compatible with one or more existing and/or standardized cartridges, thereby increasing the application range of the infusion device. Since a variety of different cartridges can be inserted, and since it is also possible for the same cartridge type to contain different substances or substances having various different concentrations, a high degree of automation and control is desirable in order to avoid mistakes not only in the dispensing steps themselves but also in the steps of preparing and correctly setting a dose.

SUMMARY

According to one embodiment, an accommodating device for a dispensing or infusion device may include a displaceable element which is displaced within the accommodating device when a cartridge is inserted into the accommodating device. Including at least one sensor which can detect the presence or absence of the displaceable element or a detection element which is disposed on or in the displaceable element.

In another embodiment, a method for detecting the presence of a cartridge in an accommodating device may include: taking an optical measurement or capacitive measurement, or both, to detect whether or not the displaceable element has a predefined position within the accommodating device; determining whether the cartridge has been inserted; and optionally detecting the type of cartridge which has been inserted.

In another embodiment, a method for operating a dispensing or infusion device may include: taking an optical measurement or capacitive measurement, or both, to detect whether or not the displaceable element has a predefined position within the accommodating device; determining whether the cartridge has been inserted, and optionally detecting the type of cartridge which has been inserted; and blocking the dispensing or infusion device from being operated if the cartridge has not been inserted.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 7A illustrates a measurement method corresponding to the alternative electronic circuit of FIG. 7B according to one or more embodiments shown and described herein;

FIG. 15 shows a cartridge detection, using a capacitive sensor according to one or more embodiments shown and described herein.

DETAILED DESCRIPTION

Figure 1:
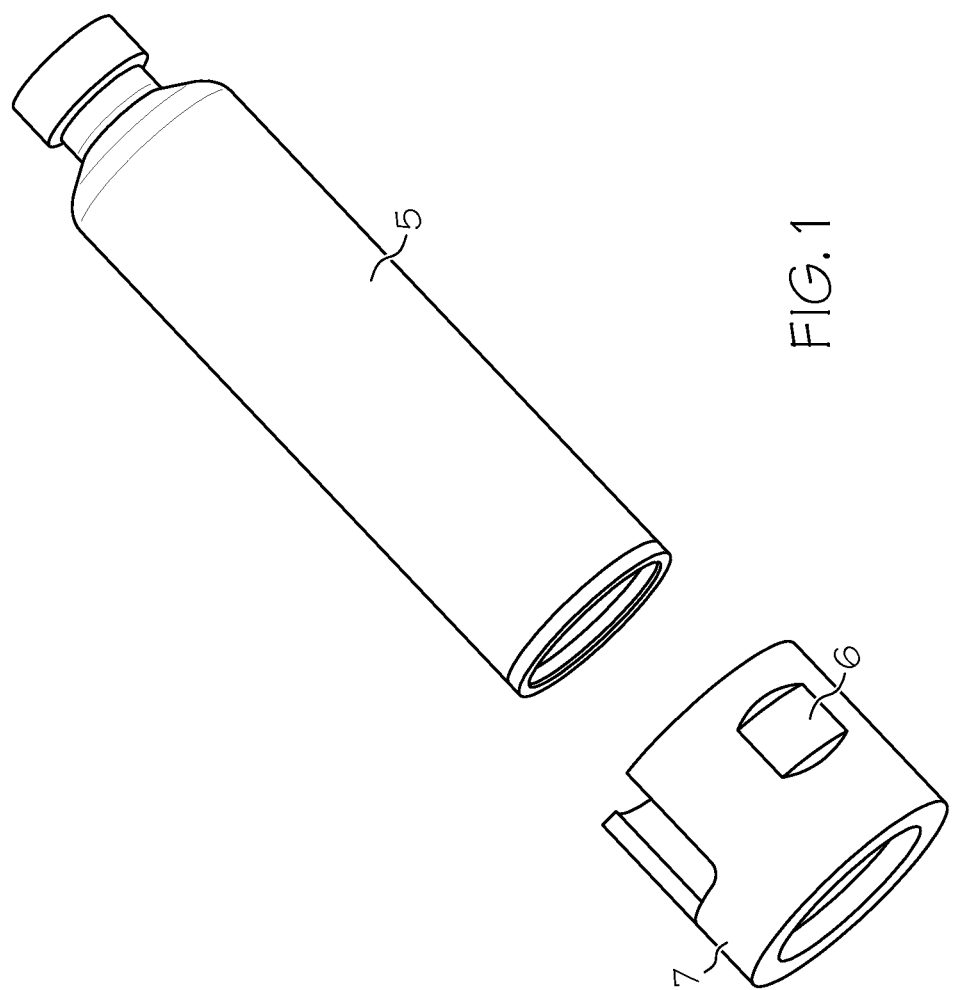
FIG. 1 shows a cartridge and a length-adjusting element according to one or more embodiments shown and described herein.

One embodiment described herein provides an accommodating device for a dispensing or infusion device and a method for detecting a cartridge, wherein the device and method enable safe and reliable operation for dispensing a substance contained in a cartridge once the cartridge has been securely inserted into the dispensing device. The dispensing device preferably includes an operating system or controller for controlling functions of the device, in accordance with the information provided by a cartridge detector which provides information as to whether or not a cartridge has been inserted, and optionally using information which specifies the type of cartridge inserted or the content of the cartridge inserted into the device, based on properties or dimensions of the cartridge such as its longitudinal length.

Another embodiment described herein relates to an accommodating device or receptacle for a cartridge or container, a receptacle in a dispensing or infusion device having a movable or displaceable element such as a length-adjusting element which can optionally be biased, for example by means of a spring, such that it is situated in an initial or unloaded position when no cartridge is inserted and is situated in a loaded position which is offset from the initial position, for example, pushed into the offset position by an inserted cartridge when the cartridge is inserted. The length-adjusting element comprises at least one detection element, for example, an element which exhibits a specified geometry or a specified optical characteristic or capacitivity or dielectric permittivity or a specific magnetic permeability or is simply in some way different to the interior of the accommodating device or from other parts of the length-adjusting element. This detection element can be detected using at least one sensor which can detect the presence or absence of the displaceable element and/or the at least one detecting element which is positioned on or connected to the length-adjusting element.

The detection element can be provided in the form of a notch or indentation on the length-adjusting element, wherein the notch or indentation can have an optical or electrical or magnetic property, such as a reflectance and/or absorbance, which is different to the rest of the length-adjusting element, so as to provide a safe and reliable detecting mechanism.

Thus, cartridge detection is performed without actually detecting the cartridge itself. Instead, the position of an element which is shifted, pushed or displaced by the cartridge is detected. This provides the advantage that the sensors or detectors can be separated or shielded from the area where the cartridge is inserted, thus protecting these elements, for example, from external contamination. Additionally, the combination of the sensor and the element being linked to the length-adjusting element is unique and allows for calibration of the sensor, which significantly increases the reliability of the detecting mechanism. A further advantage is that the element can not be modified by the user though false manipulations or other types of modifications performed by the cartridge supplier or the patient. The combination of sensor and displaceable element is unique and thus allows an individual calibration in order to compensate for manufacturing and assembly tolerances. This is not possible if the cartridge itself is detected, since the relevant properties show some variation from cartridge to cartridge.

The displaceable element and/or the at least one detection element can preferably be detected by an optical sensor, for example, a photo transistor or a photodiode based detection mechanism, and optionally a light source such as a light emitting diode (LED), for example, a surface-mounted device (SMD) LED. The accommodating device optionally comprises an optical active element, for example, a len or a diffractive element or a light guide such as an optical fiber and can be at least partially or fully transparent.

Using an optical detection mechanism provides the advantage of a safe, robust and automatic detection of whether or not a cartridge has been inserted. It also provides the advantage of being robust against water or transparent solution contaminations, for example, insulin solutions.

The controller or operating system of the dispensing device can use the above information in order, for example, to initiate an automatic resetting if a cartridge is removed, or to block the operation of the dispensing device if it is detected that no cartridge is present, to avoid a malfunction or faulty operation of the device. Additionally, the controller or operating system can modify infusion parameters depending on the cartridge or inform the patient of the insertion of wrong cartridge type. For an insulin pump, cartridges with insulin formulations of different concentrations may be available, wherein the cartridges may have different dimensions, in particular different lengths. For embodiments which allow detecting the position of the displaceable element with the cartridge being inserted, this information can be used to determine the cartridge type. An infusion parameter that would typically be adapted is the displacement of the cartridge plunger for dispensing or infusion a given amount of insulin.

While it is possible to use a single optical sensor with or without a single light source, it may be useful to provide a single light source in connection with two or more optical sensors or, in another embodiment, to provide a single optical sensor in combination with two or more light sources. Optionally, two or more sensors can be used in combination with two or more light sources.

In another embodiment, a capacitive sensor can be used with or without the above-mentioned optical sensor to detect the presence or type of a cartridge which is inserted into a dispensing or infusion device, by detecting the presence or absence of a displaceable element or shift in the displaceable element, as detailed above.

In another embodiment, the accommodating device or receptacle can be designed such that the length-adjusting element has at least one predefined position within the accommodating device or receptacle, such as a specified longitudinal position, when no cartridge is inserted. In this case, the length-adjusting element can, for example, be biased so as to be situated in an uppermost or unloaded position when no cartridge is inserted and to be situated in a position which is different to the uppermost or unloaded position when a cartridge is inserted. The length-adjusting element can have at least one other predefined position when a cartridge is inserted, which depends on the length or geometry of the cartridge. For example, the length-adjusting element is positioned in a first displaced position when a first cartridge having a first length is inserted and is positioned in a second displaced position, which is offset by a larger amount than the first position, when a cartridge of a second type which is different to the first type and has a larger longitudinal length is inserted. Since the detection element is located on or connected to the length-adjusting element, it is possible for an appropriate number of sensors, such as one, two or more sensors, to detect whether or not a cartridge has been inserted and optionally the type of cartridge which has been inserted, if different types of cartridge have different longitudinal lengths. Thus, the length of a cartridge is used to discriminate between cartridges.

In a further embodiment, the detection element provided on the length-adjusting element can have a reflectance or reflectivity which is different to the rest of the length-adjusting element and in particular different to the surface or outer side of the length-adjusting element which surrounds the detection element. The reflectance of the detection element can, for example, be above 50%, whereas the reflectance of the remaining length-adjusting element is below 50%. It is also possible to choose other values for the reflectance of the detection element, such as a reflectance of 20 to 70%, and accordingly a reflectance of 0 to 20% for the length-adjusting element, or vice versa.

Providing the detection element on the length-adjusting element is advantageous, since detection can be performed without having to detect any elements on the cartridge itself, as is known from the prior art. Instead, the manufacturer of the dispensing or infusion device can provide both the detection element and the sensor, such that coordination and calibration can be simplified and the reliability of detection can be improved.

While the mechanism for detecting the position of a length-adjusting element as described above can work with any type of cartridge, it is additionally possible to operate this mechanism in combination with a specific type of cartridge which is designed to cooperate with the detection mechanism described above. A cartridge inserted into the accommodating device can, for example, be provided with a detection element, such as a reflecting element, for example, in the form of one or more reflecting strips surrounding the cartridge, such that the presence or absence of the at least one reflecting element on the cartridge can be detected using the sensors described above. Thus, it is possible to detect not only a detection element on the length-adjusting element but also another detection element provided on the cartridge itself, such that the displacement of the length-adjusting element which indicates the insertion of a cartridge can, for example, be detected, and additionally or alternatively the presence of a cartridge and optionally the type of the inserted cartridge can additionally be detected using one or more additional detection elements provided on the cartridge itself.

Alternatively, the detection element can be composed of an optically active structure, such as a diffraction grating, a hologram or a light guide which not only modifies the reflected intensity but also the direction of the light.

The cartridge itself can comprise or be made of an at least partially transparent material, such as glass or plastic, having preferably a wavelength compatible with the detection mechanism and is preferably transparent for the wave length of the light source or light sources. Optionally, the cartridge is not transparent in the visual spectrum, but preferably transparent for the detection mechanism wavelength. The accommodating device can be made of transparent material. For the cartridge, it is not necessary because the light shall in general not go through the cartridge.

In a further embodiment, the optical detector or optical sensor is positioned within the accommodating device or cartridge holder, such that it is directed onto the length-adjusting element, in a position such that it can detect the presence or absence of a detection element of the length-adjusting element in a predefined position, and such that it is directed onto the surface of the length-adjusting element in every possible state of operation or position of the length-adjusting element. Thus, the detector can be placed at a position which does not come close to or come into contact with an inserted cartridge, such that the detection mechanism can be protected from contamination or pollution by the cartridge.

In another embodiment, the optical detector or detectors are remotely positioned, for example, close to the accommodating device. The coupling between the optical detector and the detection element can be performed by light guides.

Thus, it is possible to detect whether or not a cartridge has been inserted and/or the type of cartridge which has been inserted on the basis of a displacement or preferably a defined displacement of the length-adjusting element which can be detected, for example, using a detection element positioned on the length-adjusting element.

In accordance with another aspect of the present disclosure, is a method for detecting whether or not a cartridge has been inserted into an accommodating device or receptacle, wherein detection is performed by detecting the position of a length-adjusting element within the accommodating device or receptacle.

In one embodiment, detection is based on the presence or absence of a detection element, such that, for example, if the detection element is present in front of a sensor, it is determined that no cartridge is inserted, and if the detection element is not present in front of the sensor, for example, because the length-adjusting element has been shifted, it is determined that an inserted cartridge is present, or vice versa.

In another embodiment, if more than one optical sensor is used, the detection can be based on the presence of the detection element by one of the optical sensors. For example, if two sensors are used, two positions of the length-adjusting element can reliably be detected: one position for the cartridge inserted, wherein the detection element is in front of the first sensor, and one position for the cartridge not inserted, wherein the detection element is in front of the second sensor. This configuration allows for partial control of the optical sensor functionality.

In accordance with another aspect, the present disclosure is directed to a method for controlling the operation of a dispensing or infusion device, wherein the dispensing operation is automatically blocked if it is detected by the method described above that a cartridge is not present in the dispensing device.

In accordance with another aspect, the present disclosure is directed to a method for controlling the operation of a dispensing or infusion device, wherein the dispensing parameters are automatically updated depending on the cartridge, substance to be dispensed concentration, present in the dispensing device.

Figure 3:
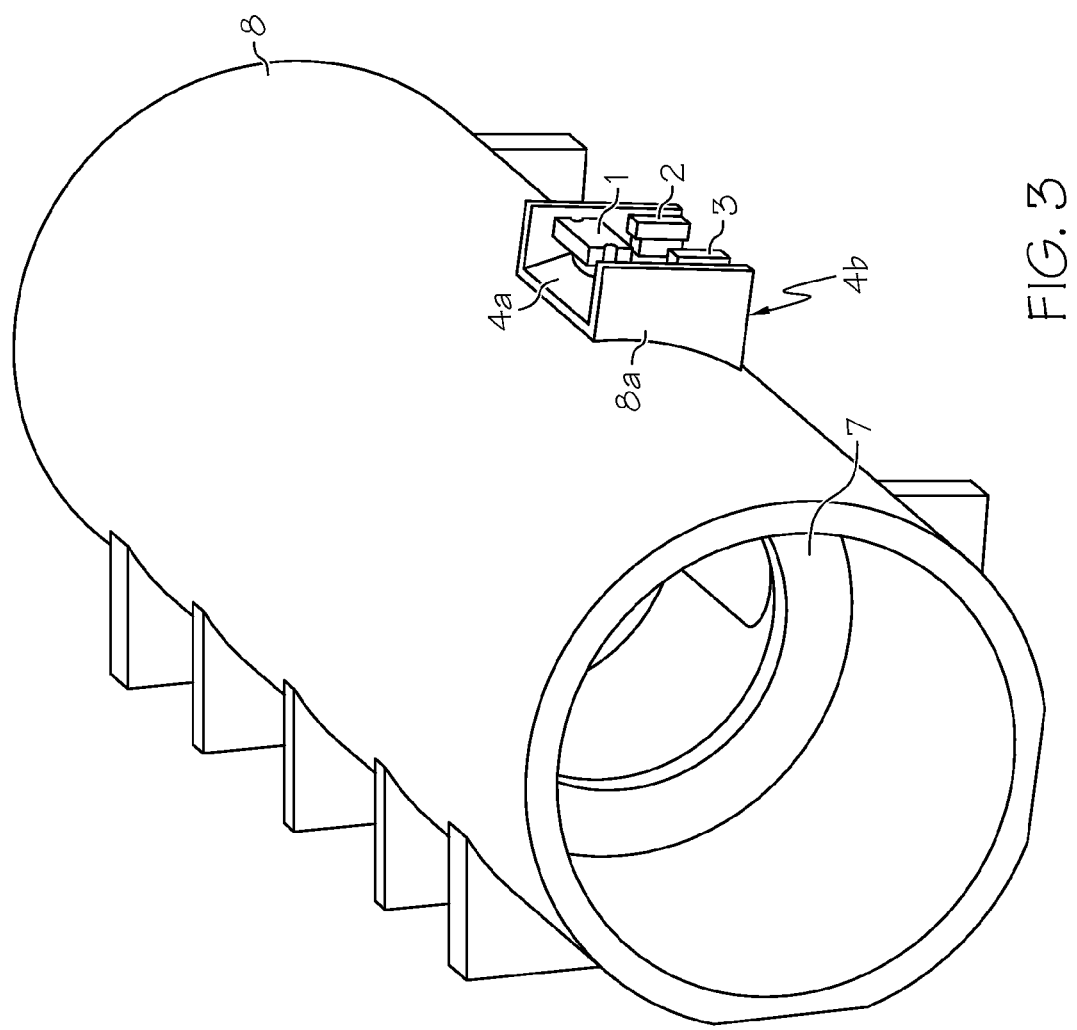
FIG. 3 shows a perspective view of an accommodating device, including the opto-electrical components of the detection mechanism according to one or more embodiments shown and described herein.

Referring now to the drawings, FIG. 1 shows a cartridge 5 which can be used as a replaceable container for a substance to be dispensed from a reusable dispensing or infusion device. The cartridge 5 can be inserted into an accommodating device 8 which is made of a transparent material and is shown in FIG. 3. Located within the accommodating device 8 is a shiftable length-adjusting displaceable element 7 which can be biased, for example, by means of a spring, counter to the insertion direction of the cartridge 5, such that the cartridge 5 acts against the force of the biasing spring when inserted, thereby displacing the length-adjusting displaceable element 7 in a longitudinal direction within the accommodating device 8. The length-adjusting displaceable element 7 has a detection element 6 on the outside of its circumferential surface, wherein the detection element 6 exhibits the shape of a notch or indentation in the embodiment shown and has a reflecting surface or, for example, a bright color such as white, contrary to the remaining surface of the length-adjusting displaceable element 7.

Figure 2:
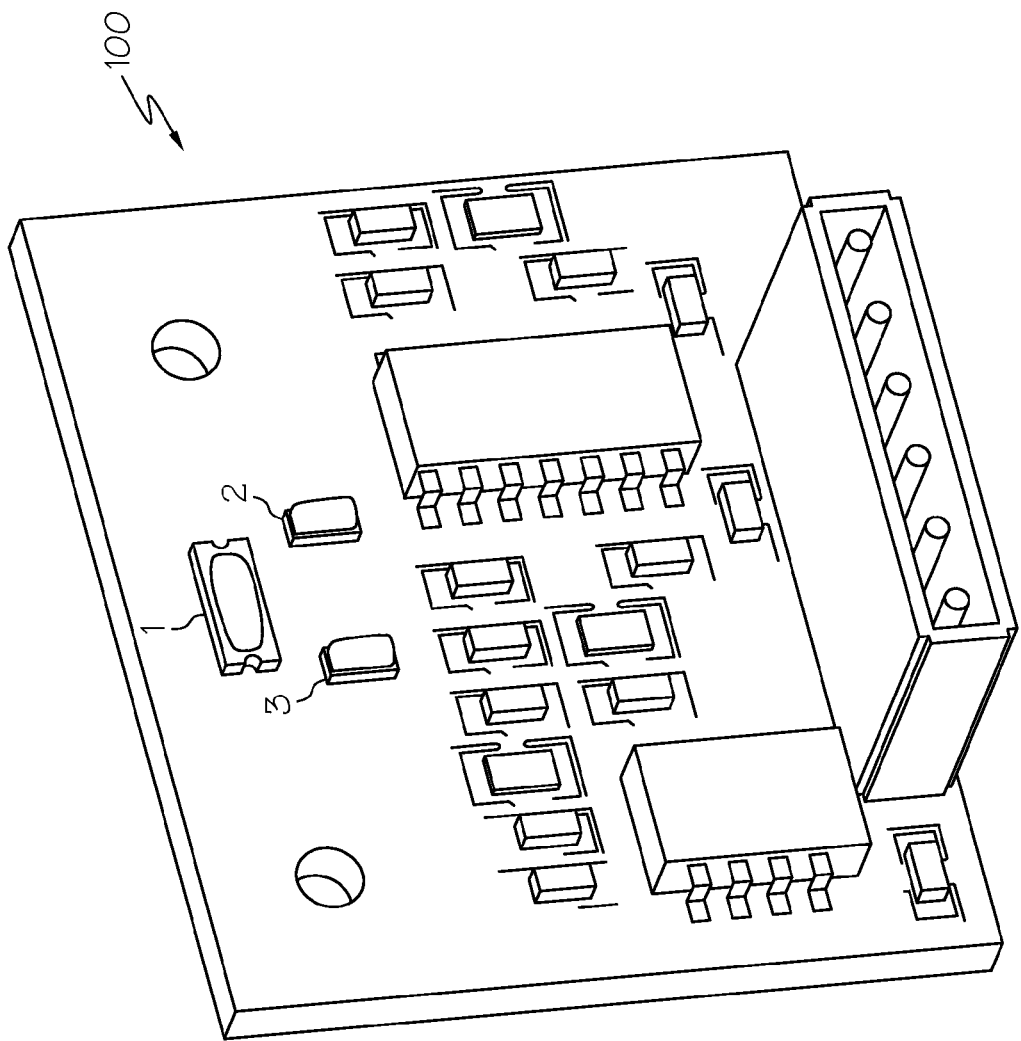
FIG. 2 shows a optoelectronic sensor unit according to one or more embodiments shown and described herein.

As shown in FIG. 3, a light source 1, which can be a light emitting diode (LED), for example, a surface-mounted device (SMD) LED, is provided on the side of the accommodating device 8, together with optical sensors 2 and 3 which act as detectors or light sensors such as optical sensors or photo transistors in order to determine whether or not a cartridge 5 has been inserted into the accommodating device 8. The light source 1 and the optical sensors 2 and 3 can be mounted on an optoelectronic sensor unit 100, as shown in FIG. 2.

The light source 1 is directed onto a light guide 4*a* which is positioned on the outer surface of the accommodating device 8 or integrated into the accommodating device 8. The optical sensors 2 and 3 face a light guide 4*b* which is positioned on the outer surface of the accommodating device 8 or integrated into the accommodating device 8. At least one light trap 8*a* can be positioned on the outside of the light source 1 and optical sensors 2 and 3 so as to shield or screen them from external light which might impair the function of the device.

Figure 5:
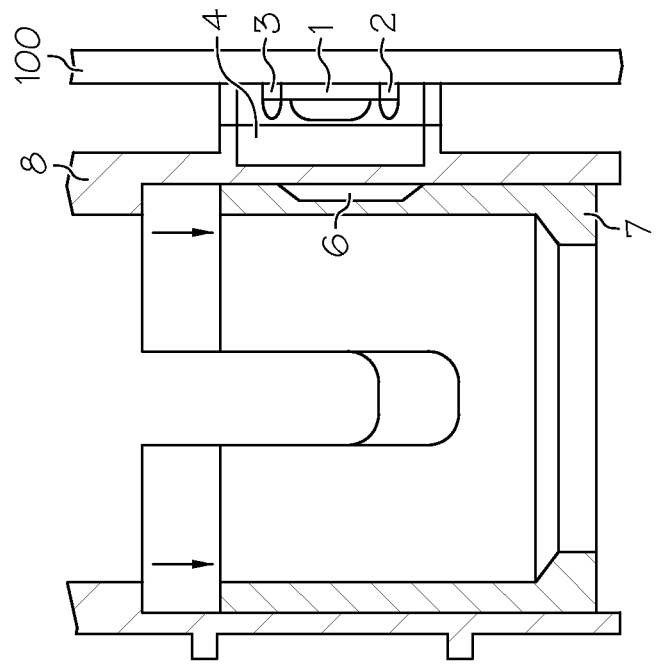
FIG. 5 shows a cross-sectional view of the accommodation device with a cartridge inserted according to one or more embodiments shown and described herein.
Figure 4:
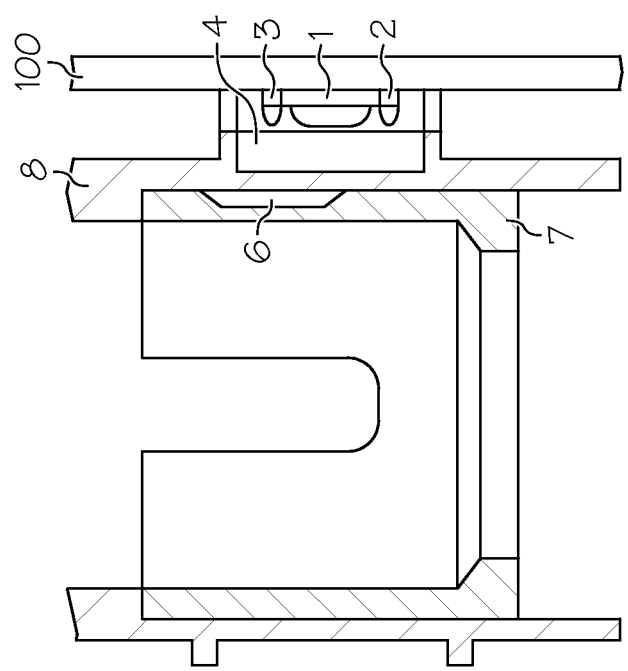
FIG. 4 shows a cross-sectional view of the accommodation device without a cartridge inserted according to one or more embodiments shown and described herein.

FIGS. 4 and 5 illustrate how the device functions. In the initial position, as shown in FIG. 4, a cartridge is not inserted into the accommodating device 8. The length-adjusting displaceable element 7 is forced into an upper or unloaded position as depicted in FIG. 4 by a biasing element or spring (not shown). When in upper or unloaded position, the detection element 6, which e.g. exhibits the shape of a notch or indentation of the length-adjusting displaceable element 7, is thus in a position such that it reflects light emitted from the light source 1 onto the optical sensor 3 only, whereas the optical sensor 2 does not receive an optical signal. Thus, it is possible to detect that no cartridge has been inserted into the accommodating device 8. The detection element 6 provided as an indentation reflects a different amount of light to the detector for two reasons: a) the indentation geometry is optimized to reflect light directly to the detector (the indentation has preferably an elliptic shape); and b) the indentation is painted with reflecting painting to locally increase the length-adjusting element reflectivity.

When or after a cartridge is inserted into the accommodating device 8, the length-adjusting displaceable element 7 is shifted to a lower or loaded position, as indicated by arrows in FIG. 5. Thus, the detection element 6 is shifted together with the length-adjusting displaceable element 7 to a position in which light emitted from the light source 1 is then reflected by the shaped of the detection element 6, i.e., the notch or indentation, onto the optical sensor 2 only, while the optical sensor 3 does not receive any light. Thus, it is possible to detect that a cartridge has been inserted into the accommodating device 8, without any direct interaction between the optical sensors 2, 3 and the cartridge 5.

Instead of using the detection element 6, which exhibits a high reflectance as compared to the surrounding area of the accommodating device 8 which has a low reflectance, as described above, the length-adjusting displaceable element 7 can also be designed to have a detection element 6 which exhibits a low reflectance and is surrounded by an area having a high reflectance. In this case, the optical sensor 2 will receive more light than the optical sensor 3 in the position shown in FIG. 4, in which a cartridge is not inserted, and the optical sensor 2 will receive less light than the optical sensor 3 in the position shown in FIG. 5, in which a cartridge is inserted.

In an intermediate position of the length-adjusting displaceable element 7 between the upper or unloaded position shown in FIG. 4 and the lower or loaded position shown in FIG. 5, both sensors will receive the same amount of reflected light, hence it is then possible to detect three different states, namely: 1. a cartridge is not inserted (FIG. 4); 2. a short cartridge is inserted, intermediate position, not shown; and 3. a long cartridge is inserted (FIG. 5).

In another embodiment, the light guides 4*a* and 4*b* (generally indicted by symbol 4 in FIGS. 4 and 5) can be designed such that a certain amount of light emitted from the light source 1 reaches both optical sensors 2 and 3. For example, when no cartridge is inserted, 20% of the emitted light reaches the optical sensor 3 and 2% reaches the optical sensor 2. Such a configuration allows a control of the sensor functionality after each measurement, as both optical sensors 2 and 3 exhibit a measurement signal.

In the above embodiment another noted advantage, and not limited thereto, is to achieve an intensity independent measurement. The light emitted from the light source 1 is reflected from the detection element 6 and reaches, according to a ratio fixed by the detection mechanism design, the optical sensors 2 and 3. The fixed ratio being independent of the absolute light intensity, light emitted or reflected, the detection mechanism is independent of the detection element 6 contamination, of the light source aging or of the photodetectors aging, under the assumption that the aging of both photodetectors is essentially similar.

Figure 3A:
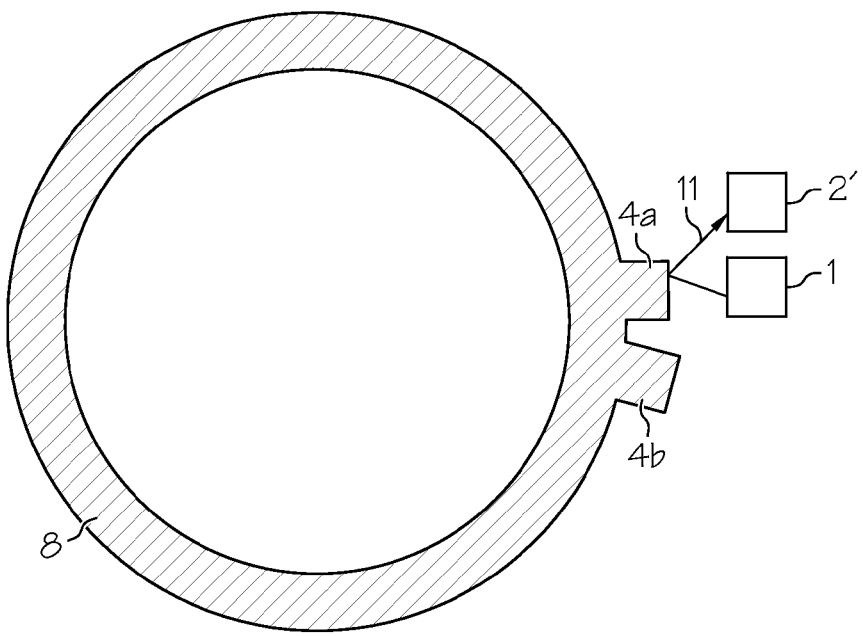
FIG. 3A shows a cross-sectional view illustrating the function of the detection mechanism according to one or more embodiments shown and described herein.

FIG. 3A shows a cross-sectional view of the accommodating device 8 interacting with a light source 1 and an additional optical sensor 2' provided to measure the light 11 emitted from the light source 1 and directly reflected on the surface of the light guide 4*a* provided on the accommodating device 8. The light intensity of the light source 1 can be measured and a loss of intensity of the light source 1, due for example, to a detected aging process. A signal can then be provided to the user, indicating that maintenance needs to be performed on the device, for example, because the light source 1 does not fully meet the system requirements or because some sort of contamination is present in the area of the optical elements such as the light source 1, light guide 4*a* and optical sensor 2'. It is possible to use the light intensity measured by the additional optical sensor 2' to adjust a threshold for evaluating, for example, the signals of the other optical sensors 2 and 3 when detecting the presence or absence of a cartridge within the accommodating device 8.

Figure 3B:
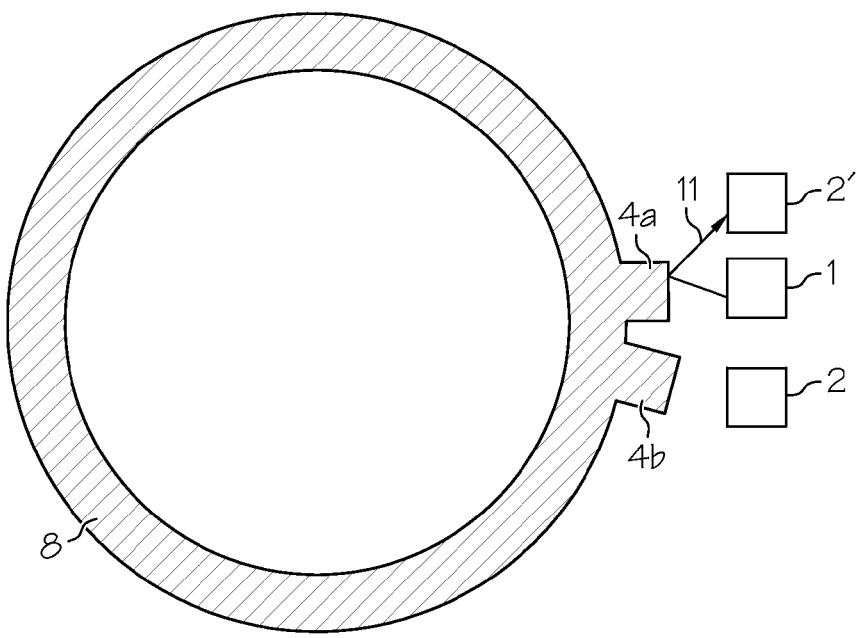
FIG. 3B shows a cross-sectional view illustrating the function of the detection mechanism according to one or more embodiments shown and described herein.

FIG. 3B illustrates another embodiment, in accordance with which the second optical sensor 3 is replaced with the optical sensor 2' which measures the light intensity of the light source 1. Such a configuration can be used for systems where contamination of the detection element 6 cannot significantly influence the measurement signal. The light path from the light source 1 to the optical sensor 2' is independent of the cartridge and allows measuring the light intensity of the light source 1, thus making the sensor less susceptible or independent to an aging process. With the ratio of light reflected onto the optical sensor 2 when a cartridge is inserted and when no cartridge is inserted being known, the cartridge presence detection is also possible.

Figure 3C:
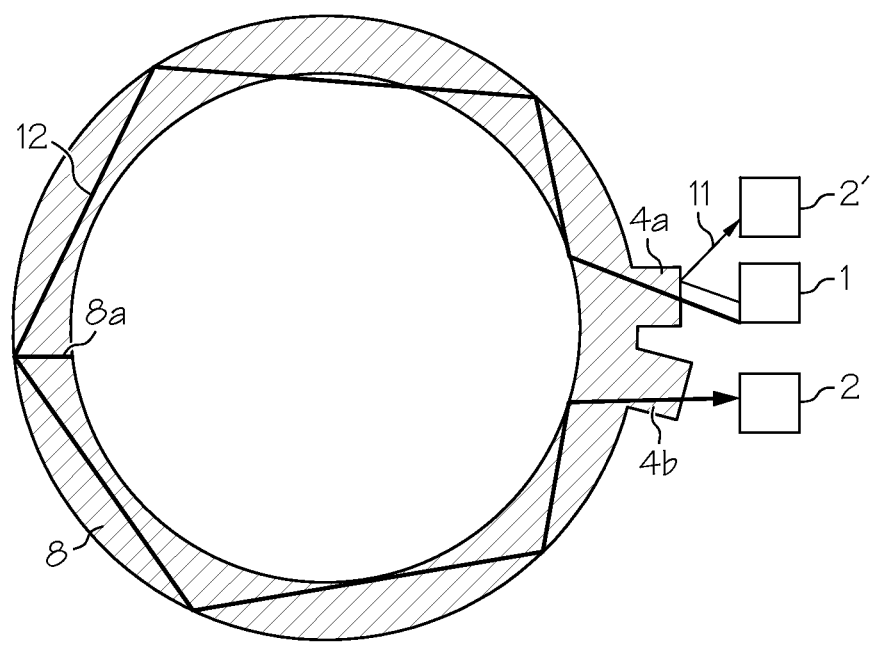
FIG. 3C shows a cross-sectional view illustrating the function of the detection mechanism according to one or more embodiments shown and described herein.
Figure 3D:
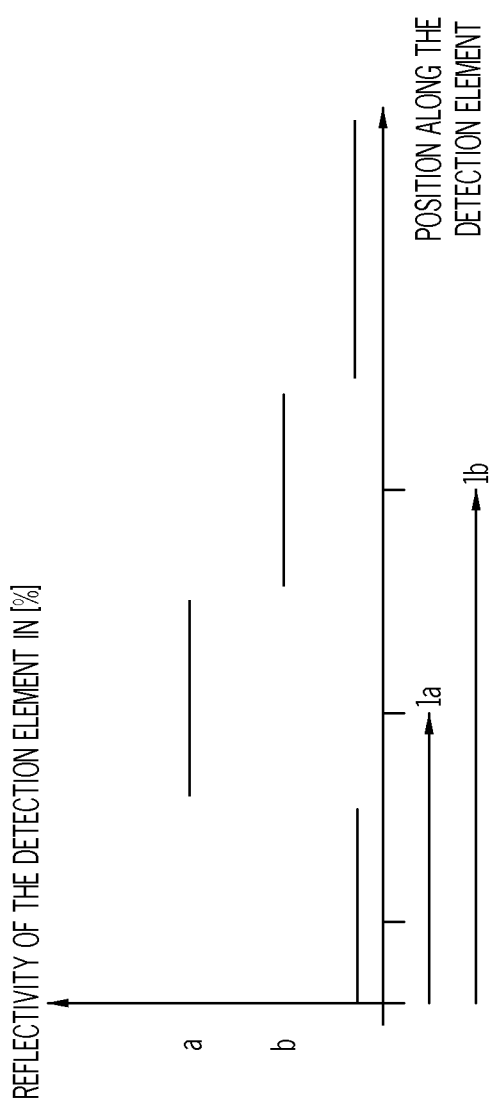
FIG. 3D illustrates an embodiment, wherein no detection element having a variable reflectivity depending on the position according to one or more embodiments shown and described herein.

In another embodiment, the length adjusting displaceable element 7 is not required to have a detection element having variable reflectivity depending on the position as illustrated in FIG. 3D. By using such a configuration, cartridges of different lengths can also be identified. For example, for a cartridge of length 1*a*, the length adjusting displaceable element 7 is displaced by the length 1*a* and due to the change in the position of the length adjusting displaceable element 7, the length adjusting displaceable element 7 reflects light having a first intensity a to the optical sensor 2. For another cartridge of length 1*b*, the length adjusting displaceable element 7 is displaced by the length 1b and due to the change in the position of the length adjusting displaceable element 7, the length adjusting displaceable element 7 reflects light having a second intensity b to the optical sensor 2. The detection mechanism is able to discriminate between the different intensities a and b and discriminate between the different cartridges.

FIG. 3C shows another embodiment of the present disclosure, in which it is possible to prevent light 12 emitted from the light source 1 from entering the transparent accommodating device 8 through the light guide 4a and being guided via various internal reflections within the transparent accommodating device 8 so as to exit through the light guide 4b. A light trap 8a, for example, in the form of a notch, gap or an opaque material is provided for this purpose.

Figure 6:
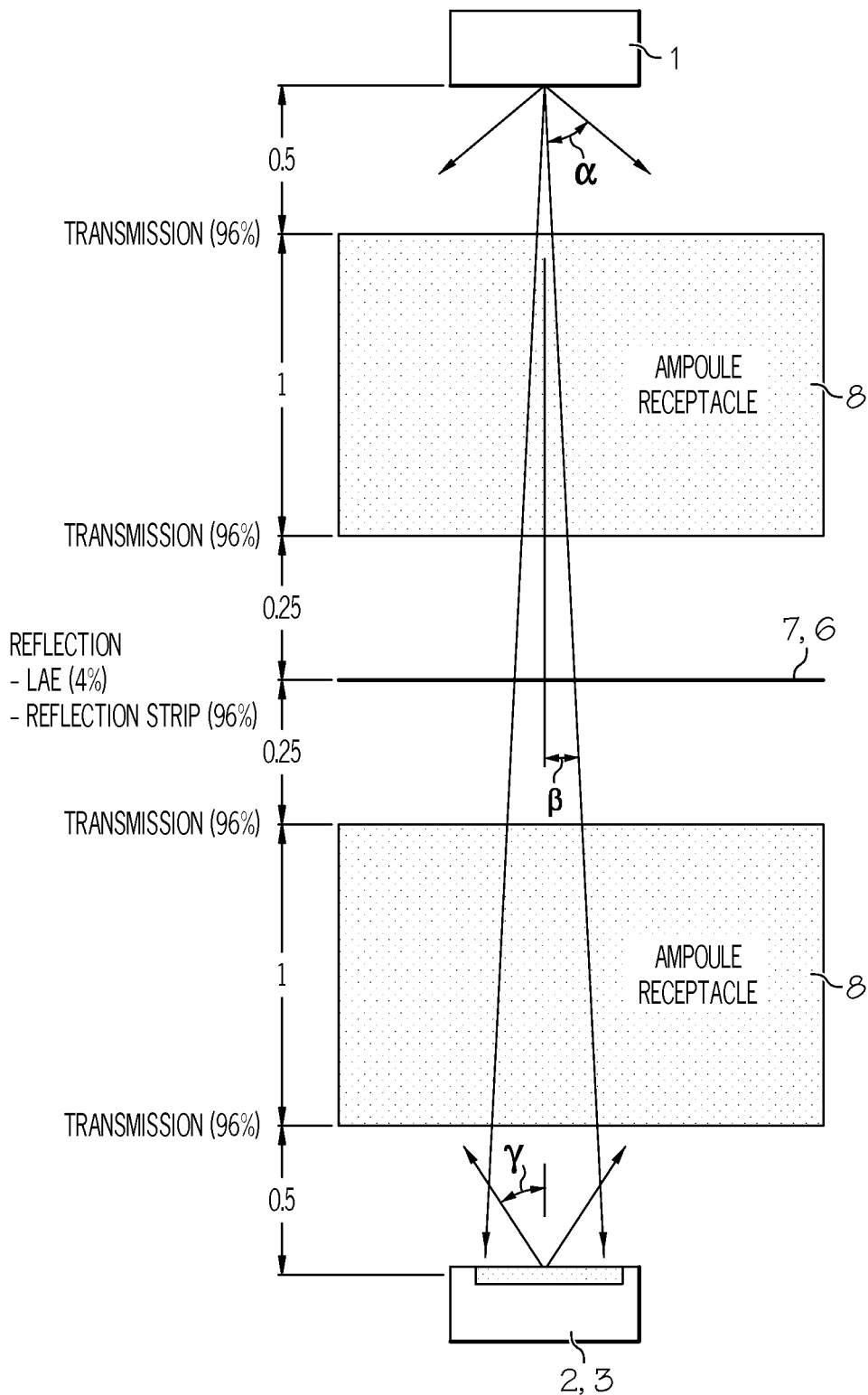
FIG. 6 illustrates the path of the light beam according to one or more embodiments shown and described herein.

FIG. 6 shows in another embodiment how the light emitted by the light source 1 enters the transparent accommodating device 8 and is reflected at the length-adjusting displaceable element 7 or the detection element 6 and transmitted back through the accommodating device 8 to reach the optical sensors 2 or 3.

Figure 7:
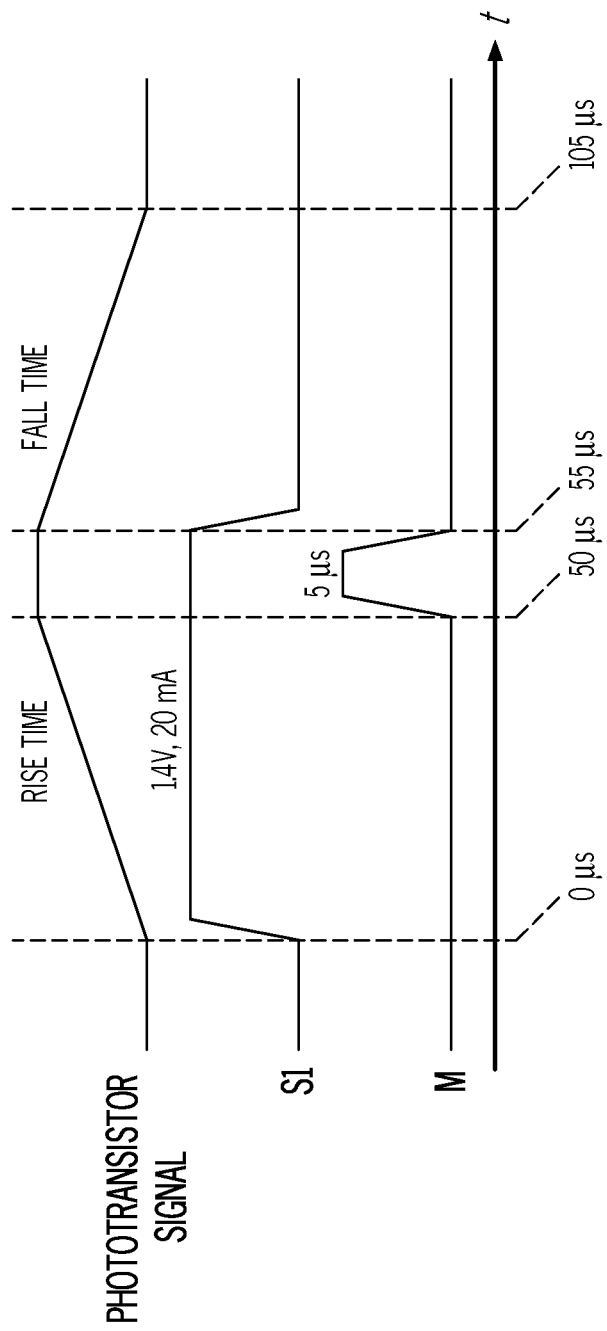
FIG. 7 illustrates how a signal is measured according to one or more embodiments shown and described herein.

FIG. 7 illustrates one example of how a signal is measured, wherein the light source 1 is activated at t=0 by switching the signal S1 from 0V to 1.4V. The signal at one of the optical sensors 2 or 3, which are embodied as a phototransistor, rises within 50 μs and then remains constant. The measurement signal M is the signal at one of the phototransistors after the rise time has elapsed and is valid for 5 μs. Once the measurement signal M has been acquired, the signal S1 for the light source 1 is deactivated and the phototransistor signal output by one of the optical sensors 2 or 3 consequently returns to 0 over a fall time of about 50 μs. The rise and fall times are exemplary, and have been chosen to accommodate the application constraints. Other rise and fall times, for example, 5 μs, can be designed if quicker measurements are needed.

The time constraints on the measurement as described above are set so as to enable an AC coupling of the measured values. This AC coupling (high-pass filter) can suppress or eliminate the influence of surrounding light, for example, daylight, which would otherwise negatively influence the function of the device. Due to the construction of the infusion device, ambient light such as sunlight or light originating from artificial light sources, can be detected by the optical sensors 2 and 3. The detected ambient light may exhibit a ratio of 1 to 10 on the optical sensors 2 and 3, causing false measurements. The maximal frequency of the ambient light being below 1 kHz and in many cases constant, the usage of an AC filter at, for example, 20 kHz with 50 μs rise and fall times reduces the impact of the ambient light on the optical sensors measurements to a negligible level.

Figure 7B:
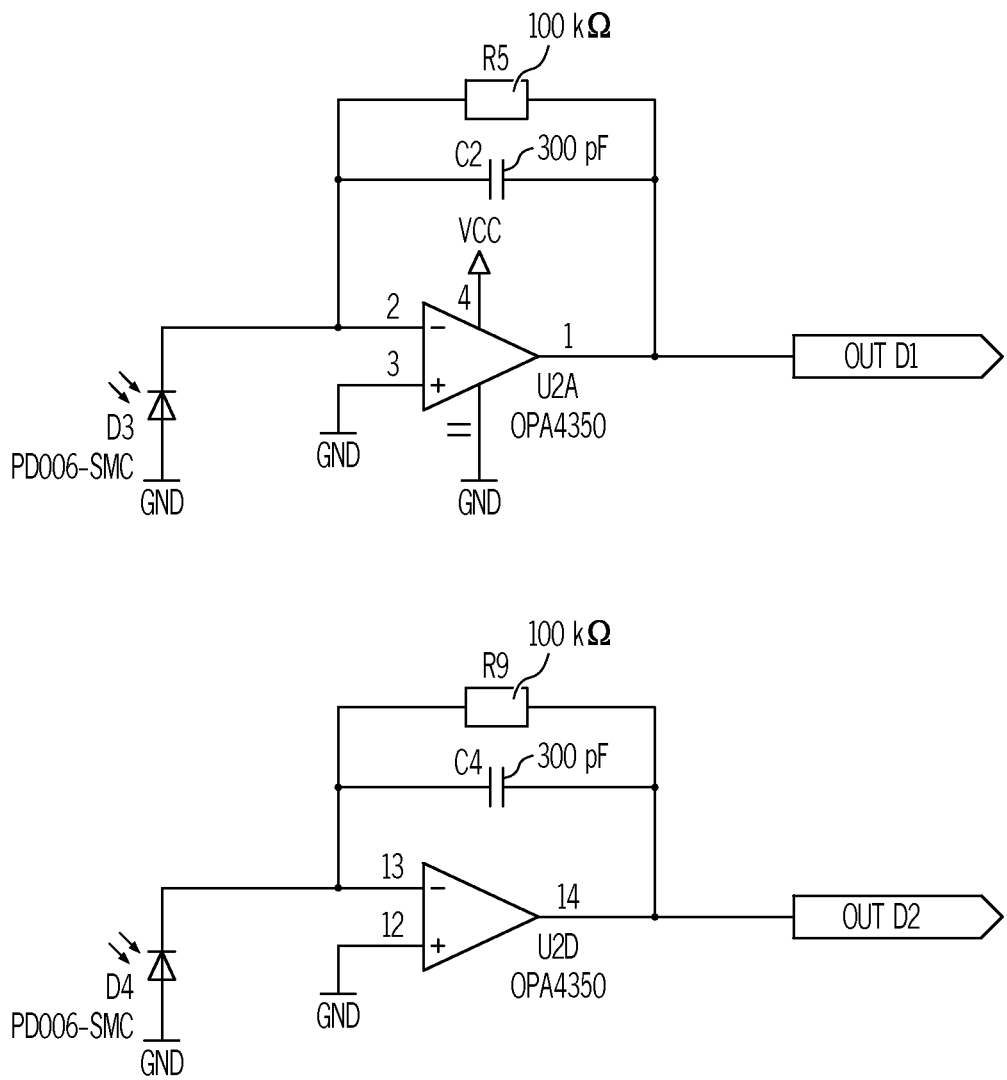
FIG. 7B illustrates the alternative electronic circuit according to one or more embodiments shown and described herein.

Another embodiment having the same ambient light independency is illustrated in FIGS. 7A and 7B. FIG. 7A illustrates an alternative signal measurement method and FIG. 7B illustrates the corresponding electronic circuit. The electronics in FIG. 7B is not AC coupled, but DC coupled. FIG. 7A illustrates a measurement method allowing reducing the ambient light intensity to a negligible level. The measurement method is composed of at least a measurement of the ambient light M1 with the light source OFF and a measurement of the signals M2 with the light source ON. By subtracting both measurements, M2−M1, a measurement independent of ambient light is obtained. FIG. 7A illustrates a measurement method with three measurements; a measurement of the ambient light M1 with the light source OFF, and a measurement of the measurement signals M2 with the light source ON, and a measurement of the ambient light M3 with the light source OFF. By subtracting M2 from (M1+M3)/2, an ambient light independent measurement is obtained.

Figure 8:
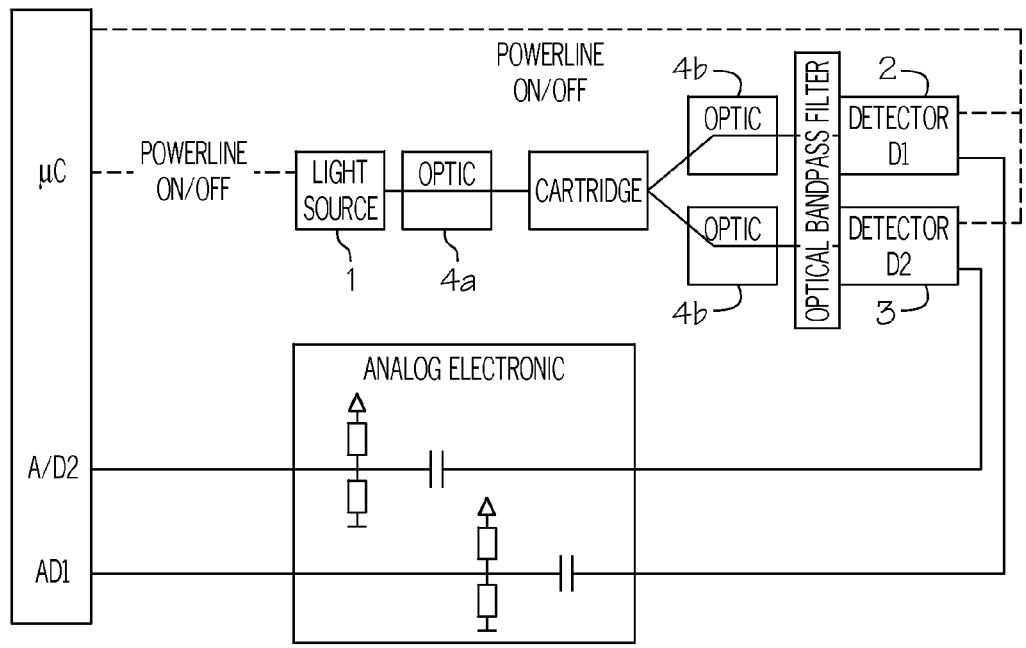
FIG. 8 illustrates a circuit according to one or more embodiments shown and described herein.

FIG. 8 shows a circuit incorporating the present disclosure. The optical bandpass filter represents the intrinsic band pass effect of the opto-electronic components, for example, the light source and phototransistors have rise and fall times which can be interpreted as band pass filters.

Figure 9:
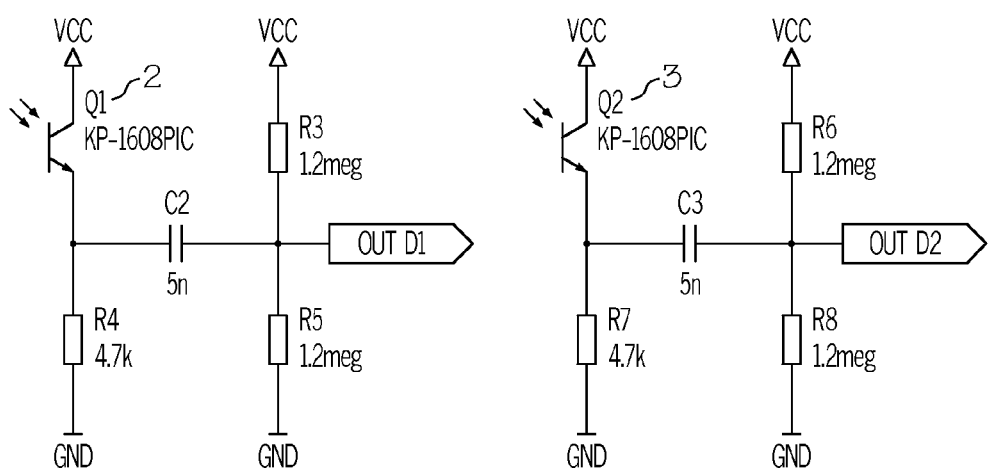
FIG. 9 illustrates circuits for connecting the optical sensors according to one or more embodiments shown and described herein.

FIG. 9 shows circuits for connecting the optical sensors 2 and 3 in order to provide output signals OUT_D1 and OUT_D2.

Figure 10:
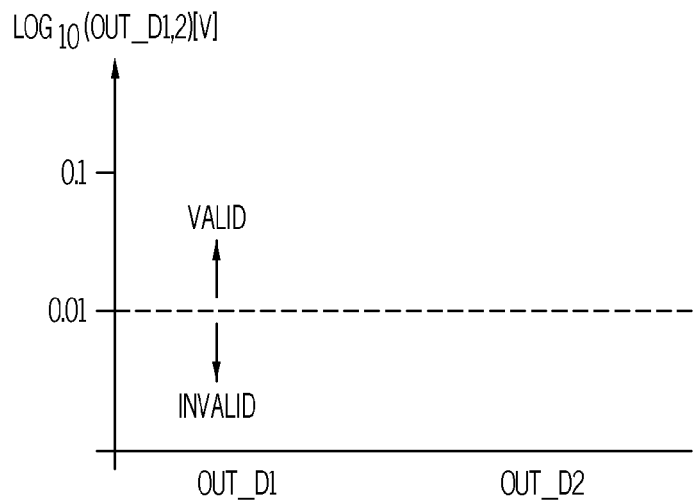
FIG. 10 illustrates an area of validity for measured signals according to one or more embodiments shown and described herein.

FIG. 10 shows how the output signals of the optical sensors 2 and 3 are evaluated. If $\text{Log}_{10}$ with measured values OUT_D1, OUT_D2 is above 0.01, the measured value is considered to be valid; if below 0.01, it is considered to be invalid.

Figure 11:
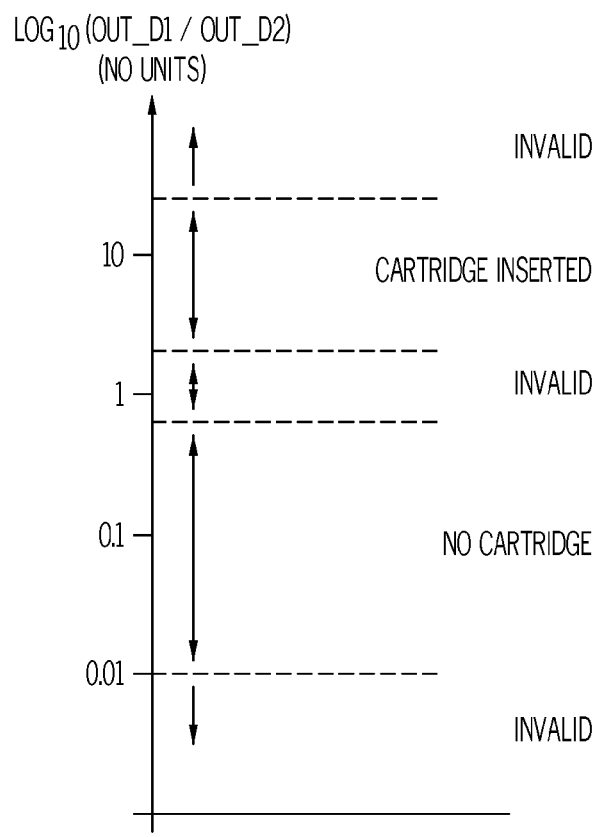
FIG. 11 illustrates how measured detector signals are analyzed according to one or more embodiments shown and described herein.

FIG. 11 illustrates how measured detector signals are analyzed in the embodiment shown in FIGS. 4 and 5, wherein $\text{Log}_{10}$ with measured values OUT_D1/OUT_D2 is determined and if this value is around 10, it is determined that a cartridge has been inserted, and if it is around 0.1, it is determined that a cartridge has not been inserted. If the value is around 1, significantly above 10 or significantly below 0.01, it is determined that the measured values are invalid.

Figure 12:
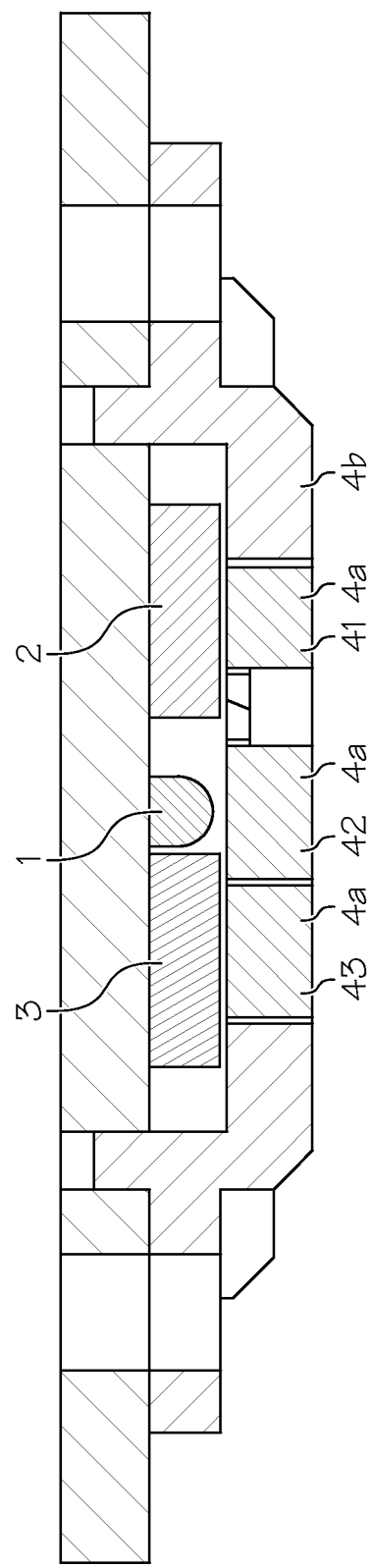
FIG. 12 shows a detection system according to one or more embodiments shown and described herein.

FIG. 12 shows another embodiment of a detection system which enables at least two different types of cartridge to be detected.

The principle of detection in accordance with this embodiment is not an absolute measurement of a reflected light intensity but rather a relative measurement of the intensity measured by the optical sensors 2 and 3. The cartridge 5 has a homogenous reflectivity distributed over the entire outer surface of the cartridge 5. If a cartridge 5 is not inserted, the reflection of the accommodating device 8 is homogenous. If the dimensions or geometry of the light guides 4a and 4b are selected appropriately, an asymmetry in the relative intensities measured (optical sensor 2/optical sensor 3) can be generated between the state "cartridge not inserted" and the state "cartridge inserted". These asymmetric relative intensities can be used to realize detection. The light guide 41 (generally indicted by symbol 4a) shown in FIG. 12 can, for example, have a diameter of 1.8 mm and a height of 1.5 mm, whereas the light guides 42 and 43 (generally indicted by symbol 4a) each have a diameter of 2.4 mm and a height of 1.5 mm. In the state "cartridge not inserted", the intensities measured by both optical sensors 2 and 3 are reflected by the accommodation device 8. Using an adequate light path design, both intensities can be designed to be equal. The distance between the light guides, from the light guides to the accommodation device and the geometry of the light guides allow achieving equal intensities, variation of any of the parameters generates an asymmetry in the detected intensities. In the state "cartridge inserted", the intensities measured by the optical sensors 2 and 3 are reflected by the accommodation device 8 and the cartridge. Using an adequate design, the intensities reflected from the cartridge can be designed to dominate the intensities reflected from the accommodation device 8. As the distance from the light guides to the cartridge is larger than the distance from the light guides to the accommodation device, the intensities detected by the optical sensors 2 and 3 from the cartridge are asymmetric.

If two different types of cartridge are used, for example, a glass cartridge and a plastic cartridge or two cartridges of the same type and optionally the same length but with different contents, an identification can be provided on one of the different types of cartridge, for example, a reflective element or imprint on one of the at least two different types, for example, on the plastic cartridge.

Figure 13:
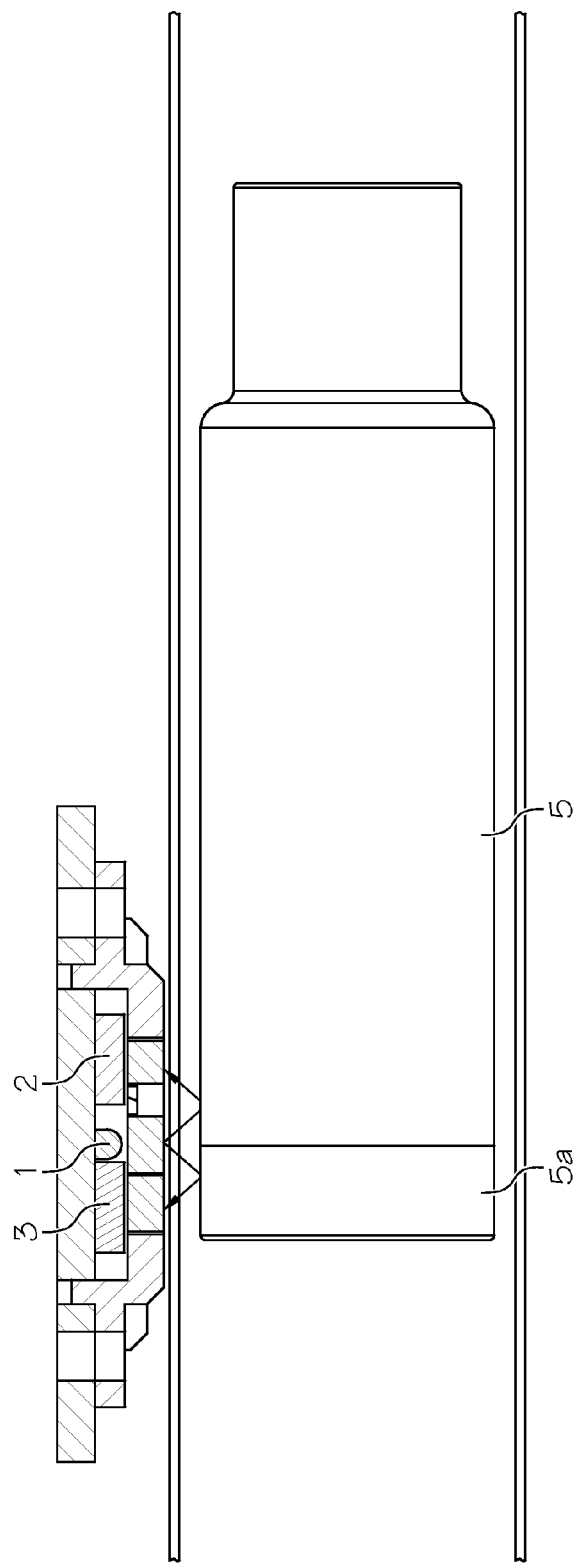
FIG. 13 shows how the device of FIG. 12 functions according to one or more embodiments shown and described herein.

In accordance with another embodiment as shown in FIGS. 13 and 14, a reflective element 5a, for example, a white or reflective strip can be provided on the outer surface of a cartridge 5 and detected, for example, by the optical sensor 3 once the cartridge 5 has been inserted into the accommodating device 8, if the accommodating device 8 is completely or at least partially transparent, as described above. Thus, it is possible to detect not only the presence or absence of the detecting element 6 which exhibits the shape of a notch or indentation provided on the length-adjusting displaceable element 7 but also the presence or absence of an optically active or reflective element 5a on the outside of an inserted cartridge 5, if said optically active surface is located in front of at least one of the optical sensors 2 and 3 once inserted.

If a cartridge 5 having a reflective element 5a is inserted into the accommodating device 8, as shown in FIG. 13, more light is reflected onto the optical sensor 3 and it is thus possible to positively determine the type of cartridge which has been inserted, using the reflective element 5a.

This measurement can be combined with a previous measurement for compensating for an offset in order to eliminate the effects of external light. The measured values of both the optical sensors 2 and 3 are first read off while the light source 1 is switched off. These previously measured offset signals can then be subtracted from subsequently measured signals in order to improve the reliability of measurements.

FIG. 13 shows an embodiment for detecting different types of cartridge, wherein one cartridge type has a reflective element 5a located at the bottom of the respective cartridge 5 and the other cartridge type has no reflective element 5a. As shown in FIG. 13, light emitted from the light source 1 is reflected by the outer surface of the cartridge 5 onto the first optical sensor 2 and by the reflective element 5a onto the second optical sensor 3. Since the reflectance of the outer surface of the cartridge 5 is different to the reflectance of the reflective element 5a, the signals measured by the optical sensors 2 and 3 will be significantly different as compared to the situation in which a cartridge 5 which has no reflective element 5a inserted, in which case both optical sensors 2 and 3 will measure essentially the same signal. The presence or absence of the additional reflective element 5a on a cartridge 5 can be determined, and it is thus possible to distinguish between the two different types of cartridge.

Figure 14A:
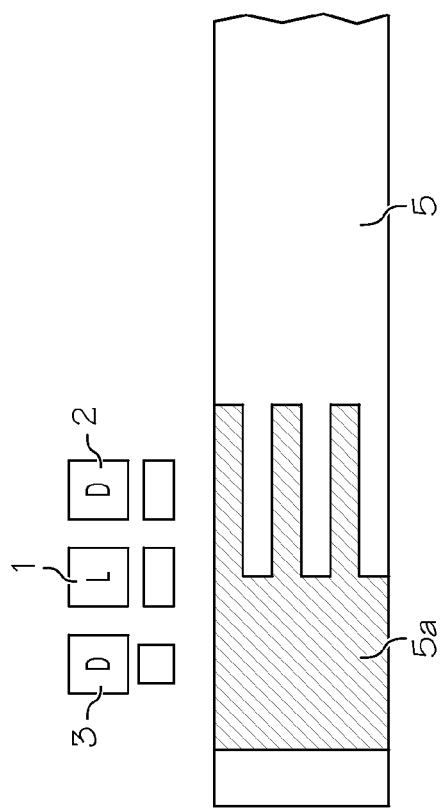
FIG. 14A shows a sensor array on a cartridge according to one or more embodiments shown and described herein.
Figure 14B:
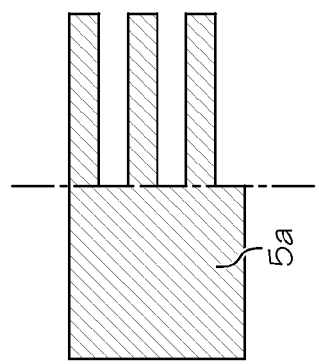
FIG. 14B shows a sensor array on a cartridge according to one or more embodiments shown and described herein

FIG. 14A shows another embodiment, in which a reflective element 5a which has a reflective surface is provided on a cartridge 5 and comprises a first area on the left-hand side, shown in detail in FIG. 14B, which exhibits an approximately 100% reflective surface, whereas on the right-hand side in FIG. 14B, only 50% of the surface of the cartridge is covered by the reflective element 5a, thus providing about 50% overall reflectivity if the outer surface of the cartridge 5 has essentially zero reflectivity. Using this or similar forms of a marking or reflective element 5a, it is possible to distinguish between two or more different types of cartridge. For example, another cartridge can exhibit a reflective surface on the left hand side with approximately 30% reflectivity and the reflective surface on the right hand side with approximately 65% reflectivity. The method described is also based on relative light intensity measurement and requires that the two reflective surfaces are detected by the optical sensors 2 and 3. The measurement is also independent of aging of the light source.

FIG. 15 shows another embodiment of an accommodating device 8 which enables the longitudinal position of the length-adjusting displaceable element 7 within the accommodating device 8 to be detected using capacitive sensors C1 and C2. In the initial state shown in Position 1 on the left in FIG. 15, the length-adjusting displaceable element 7 is biased by means of a spring, not shown, into an uppermost position located between the capacitive sensors or capacitors C1. If a cartridge 5' of a first type having a specific length is inserted into the accommodating device 8, the cartridge 5' acts against the biasing force on the length-adjusting displaceable element 7, resulting in a shift in the length-adjusting displaceable element 7 when the cartridge 5' is inserted, to a position between the capacitive sensors or capacitors C1 and C2, as shown in Position 2.

If a cartridge 5" of a second type having a greater length than the length of the cartridge 5' of the first type is inserted into the accommodating device 8, the length-adjusting displaceable element 7 is displaced even further, into a position adjacent to the capacitive sensor C2, as shown in Position 3.

Using the principles or apparatus or method explained in WO 2006/021295 A1, the teaching of which with respect to detecting the position of a shiftable element is hereby incorporated by reference, the position of the length-adjusting element with respect to the accommodating device 8 or with respect to capacitive sensors C1 and C2 located at a fixed position with respect to the accommodating device 8 and therefore the length of the fully inserted cartridges 5' and 5" can be determined, so as to detect the type of cartridge. It is also possible to detect that a cartridge is not present, if the biased length-adjusting displaceable element 7 is in Position 1 as shown on the left in FIG. 15.

Figure 16:
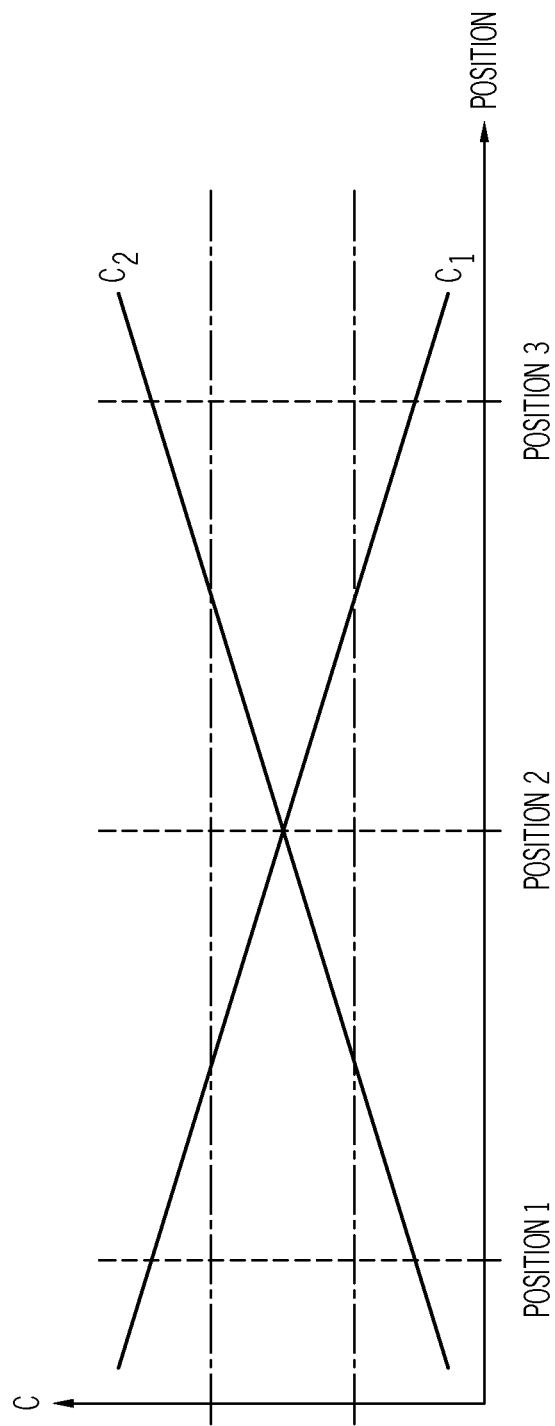
FIG. 16 shows how the capacitive detection system shown in FIG. 15 functions according to one or more embodiments shown and described herein.

FIG. 16 shows the output of the capacitive sensors C1 and C2 for Positions 1 to 3 as illustrated in FIG. 15. If the length-adjusting displaceable element 7 has a high dielectricity, the capacitive sensor C1 measures a high capacitance in Position 1 and the capacitive sensor C2 measures a low capacitance in Position 1, since the length-adjusting displaceable element 7 is located between the capacitive sensor or capacitor C1. In Position 2, both capacitive sensors or capacitors C1 and C2 measure essentially the same signal or capacitance. In Position 3, in which the length-adjusting displaceable element 7 is shifted to a position between the capacitive sensor or capacitor C2, the measured signal or capacitance C2 is large as compared to the measured signal C1.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. An accommodating device capable of accommodating cartridges of different lengths from each other for a dispensing or infusion device, the device comprising:
   a displaceable element comprising a detection element disposed thereon wherein the displaceable element is configured to be displaced within the accommodating device when one of the cartridges is inserted into the accommodating device; and
   at least one sensor configured to detect a position of the detection element based on the displacement of the displaceable element when the one of the cartridges is inserted into the accommodating device;
   wherein the at least one sensor is located at a fixed position with respect to the displaceable element which is a length-adjustable element, and the accommodating device is configured to determine the position of the length-adjustable element and determine the length of the one of the cartridges when fully inserted to detect the type of the inserted cartridge.

2. The device according to claim 1, wherein the at least one sensor comprises at least one light source and at least one optical sensor, and wherein the at least one light source and the at least one optical sensor are stationary with respect to the accommodating device or connected to the accommodating device.

3. The device according to claim 1, wherein the at least one sensor comprises two or more optical sensors or two or more capacitive sensors or combinations thereof, and further comprising two or more light sources.

4. The device according to claim 1, wherein the accommodating device is at least partially made of a transparent material.

5. The device according to claim 1, further comprises at least one light guide positioned on the outer surface of the accommodating device.

6. The device according to claim 5, wherein the at least one sensor comprises at least one optical sensor and wherein the at least one light guide is configured to face the at least one optical sensor, a light source, a filter, or combinations thereof to reduce or eliminate ambient light being directed on the at least one optical sensor.

7. The device according to claim 1, wherein the accommodating device and the displaceable element have an essentially cylindrical shape.

8. The device according to claim 1, wherein the displaceable element is connected to a biasing element in order to bias the displaceable element into a defined or unloaded position when the cartridge is not inserted and when the cartridge is inserted the displaceable element is displaced longitudinally into a loaded position.

9. The device according to claim 1, wherein the detection element on the displaceable element is a notch or indentation.

10. The device according to claim 1, wherein the detection element has a reflectance which is different to the reflectance of the surrounding surface of the displaceable element.

11. The device according to claim 1, wherein the accommodating device comprises at least one light trap for preventing light from being guided from an entry point to an exit point completely within the accommodating device.

12. A method for detecting the presence of a cartridges of different lengths from each other in an accommodating device, the method comprising:
provide a displaceable element comprising a detection element thereon wherein the displacement element is configured to be displaced within the accommodating device when one of the cartridges is inserted into the accommodating device;
inserting the cartridge into the accommodating device;
taking an optical measurement or capacitive measurement, or both, with at least one sensor to detect at least one predefined position of the displaceable element;
determining whether the one of the cartridges has been inserted based on the at least one predefined position of the displaceable element; and
detecting the type of cartridge which has been inserted;
wherein the at least one sensor is located at a fixed position with respect to the displaceable element which is a length-adjustable element, and the accommodating device is configured to determine the position of the length-adjustable element and determine the length of the one of the cartridges when fully inserted to detect the type of the inserted cartridge.

13. The method for detecting the presence of a cartridge according to claim 12, further comprising taking an optical reference measurement with a light source deactivated prior to taking the optical reference measurement with the light source activated.

14. The method for detecting the presence of a cartridge according to claim 12, wherein light reflected by the displaceable element is detected by two sensors and the at least one predefined position of the displaceable element is determined using a ratio of signal values of the two sensors.

15. The method according to claim 12, wherein the at least one predefined position comprises an unloaded position when the cartridge is not inserted, a first displaced position and a second displaced position when the cartridge is inserted, the second displacement position being different from the first displacement position based on the length of the cartridge.

16. A method for operating a dispensing or infusion device capable of accommodating cartridges of different lengths from each other, the method comprising:
providing a displaceable element comprising a detection element thereon wherein the displaceable element is configured to be displaced within the accommodating device when one of the cartridges is inserted into the accommodating device;
taking an optical measurement or capacitive measurement, or both, with at least one sensor to detect a predefined position of the displaceable element within the accommodating device;
determining whether a cartridge has been inserted based on the predefined position of the displaceable element;
inserting the cartridge into the accommodating device and detecting the type of cartridge which has been inserted; and
blocking the dispensing or infusion device from being operated if the cartridge has not been inserted;
wherein the at least one sensor is located at a fixed position with respect to the displaceable element which is a length-adjustable element, and the accommodating device is configured to determine the position of the length-adjustable element and determine the length of the one of the cartridges when fully inserted to detect the type of the inserted cartridge.

17. The method according to claim 16, wherein the predefined position comprises an unloaded position when the cartridge is not inserted, a first displaced position and a second displaced position when the cartridge is inserted, the second displacement position being different from the first displacement position based on the length of the cartridge.

* * * * *

UNITED STATES PATENT AND TRADEMARK OFFICE
CERTIFICATE OF CORRECTION

PATENT NO. : 8,902,433 B2
APPLICATION NO. : 12/948385
DATED : December 2, 2014
INVENTOR(S) : Andreas Schlaeppi et al.

It is certified that error appears in the above-identified patent and that said Letters Patent is hereby corrected as shown below:

Specification

Col. 4, Line 10,
"prises an optical active element, for example, a len or a dif-" should read
--prises an optical active element, for example, a lens or a dif- --;

Col. 4, Lines 33-34,
"displacement of the cartridge plunger for dispensing or infusion a given amount of insulin." should read --displacement of the cartridge plunger for dispensing or infusing a given amount of insulin.--;

Col. 8, Line 7,
"ally indicted by symbol 4 in FIGS. 4 and 5) can be designed" should read
--ally indicated by symbol 4 in FIGS. 4 and 5) can be designed--;

Col. 10, Line 40,
"indicted by symbol 4a) shown in FIG. 12 can, for example," should read
--indicated by symbol 4a) shown in FIG. 12 can, for example,--; and Col. 10, Line 42,
"the light guides 42 and 43 (generally indicted by symbol 4a)" should read
--the light guides 42 and 43 (generally indicated by symbol 4a)--.

Signed and Sealed this
Fifth Day of January, 2016

Michelle K. Lee
*Director of the United States Patent and Trademark Office*